(12) United States Patent
Saghatchi et al.

(10) Patent No.: US 11,684,458 B2
(45) Date of Patent: Jun. 27, 2023

(54) ACCURACY OF ELECTROMAGNETIC NAVIGATION SYSTEMS

(71) Applicants: Samaneh Saghatchi, Zanjan (IR); Javad Hasani Bidgoli, Tehran (IR); Mohammad Jalal Sadeghi, Tehran (IR); Alireza Ahmadian, Tehran (IR); Farzam Farahmand, Tehran (IR); Saeed Sarkar, Tehran (IR)

(72) Inventors: Samaneh Saghatchi, Zanjan (IR); Javad Hasani Bidgoli, Tehran (IR); Mohammad Jalal Sadeghi, Tehran (IR); Alireza Ahmadian, Tehran (IR); Farzam Farahmand, Tehran (IR); Saeed Sarkar, Tehran (IR)

( * ) Notice: Subject to any disclaimer, the term of this patent is extended or adjusted under 35 U.S.C. 154(b) by 929 days.

(21) Appl. No.: 16/511,343

(22) Filed: Jul. 15, 2019

(65) Prior Publication Data

US 2019/0350685 A1   Nov. 21, 2019

Related U.S. Application Data

(60) Provisional application No. 62/698,158, filed on Jul. 15, 2018.

(51) Int. Cl.
| | | |
|---|---|---|
| *A61B 5/00* | (2006.01) | |
| *A61C 8/00* | (2006.01) | |
| *A61B 5/06* | (2006.01) | |
| *A61B 90/50* | (2016.01) | |
| *A61B 34/20* | (2016.01) | |
| *A61B 34/30* | (2016.01) | |

(52) U.S. Cl.
CPC ............ *A61C 8/0089* (2013.01); *A61B 5/062* (2013.01); *A61B 90/50* (2016.02); *A61B 2034/2051* (2016.02); *A61B 2034/304* (2016.02)

(58) Field of Classification Search
CPC . A61B 2034/2051; A61B 5/062; A61B 90/50; A61B 34/20
See application file for complete search history.

(56) References Cited

U.S. PATENT DOCUMENTS

| | | | | |
|---|---|---|---|---|
| 2009/0209852 A1* | 8/2009 | Mate | .................... | A61B 90/39 600/431 |
| 2014/0066701 A1* | 3/2014 | Wilson | ............. | A61B 1/000094 600/102 |
| 2014/0350387 A1* | 11/2014 | Siewerdsen | ............ | A61B 6/583 600/436 |

\* cited by examiner

*Primary Examiner* — Rajeev P Siripurapu
(74) *Attorney, Agent, or Firm* — Bajwa IP Law Firm; Haris Zaheer Bajwa

(57) ABSTRACT

A system for electromagnetic navigation in dental implant placement may include an electromagnetic tracking system that may be configured to track positions and orientations of a plurality of electromagnetic sensors. An exemplary electromagnetic tracking system may include a field generator that may be attached to a dental unit utilizing a positioning arm. An exemplary system may further include a control unit that may be coupled to the electromagnetic tracking system and the positioning arm. The control unit may be configured to receive the tracked positions of the plurality of the electromagnetic sensors from the electromagnetic tracking system and to adjust at least a position or an angular orientation of the field generator to maintain the plurality of the electromagnetic sensors within a volume of interest within the tracking volume.

11 Claims, 13 Drawing Sheets

ACCURACY OF ELECTROMAGNETIC NAVIGATION SYSTEMS

CROSS-REFERENCE TO RELATED APPLICATION

This application claims the benefit of priority from U.S. Provisional Patent Application Ser. No. 62/698,158, filed on Jul. 15, 2018, and entitled "ELECTROMAGNETIC NAVIGATION FOR DENTAL IMPLANT PLACEMENT," which is incorporated herein by reference in its entirety.

TECHNICAL FIELD

The present disclosure relates to systems and methods for electromagnetic navigation in dentistry, particularly relates to systems and methods for electromagnetic navigation in dental implant surgery, and more particularly relates to systems and methods for improving the accuracy of electromagnetic navigation systems utilized in dental implant placement.

BACKGROUND

Accurate dental implant placement is crucial in dental implant surgery to ensure a precise dental restoration. Accurate dental implant placement may prevent intraoperative damages to critical anatomic structures, such as nerves. Image-guided surgical placement of dental implants may be utilized to improve the accuracy of placement of dental implants, which in turn improves the accuracy of dental restoration.

In an image-guided surgical placement of dental implants, a computed tomography (CT) or a cone-beam computed tomography (CBCT) of an oral cavity of a patient may be uploaded to a navigation software of a surgical navigation system. The surgical navigation system may then be utilized for tracking a tip of a surgical tool during surgery and mapping the tracked tip of the surgical tool on the uploaded CT or CBCT, which may allow a surgeon to visually observe and follow the tip of the surgical tool in real time. A tracking reference component may be attached to a surgical tool that may allow its position and orientation to be tracked. Another tracking reference component may be fixed to a tooth, gum, or jawbone of a patient that may allow determining the position and orientation of a patient's head, i.e., a surgical site.

Surgical navigation systems may perform surgical tool motion tracking utilizing tracking systems, such as optical tracking systems and electromagnetic tracking systems. In optical tracking systems, tracking reference components may be optical markers. An optical marker may be attached to a surgical tool, and precise orientation and motion of the optical marker may be observed by multiple cameras. In electromagnetic tracking systems, tracking reference components may be electromagnetic sensors. An electromagnetic sensor may be attached to a surgical tool and an electromagnetic field generator may be placed near a surgical site to establish a coordinate space. A position and orientation of the first electromagnetic sensor may then be observed within the coordinate space.

Although optical tracking systems may be more accurate than electromagnetic tracking systems, a need for maintaining continuous visibility of the optical markers and larger sizes of the optical markers in comparison with electromagnetic markers may make it challenging to utilize optical tracking systems in a dental implant surgical procedure. Since the visibility of markers is not a factor in electromagnetic tracking systems and weights and sizes of the electromagnetic sensors are negligible, electromagnetic tracking systems may be considered as promising alternative tracking systems in dental implant surgeries.

An area around a field generator of an electromagnetic tracking system is called a tracking volume of that electromagnetic tracking system. In a tracking volume of an electromagnetic tracking system, an electromagnetic sensor may be tracked. However, one drawback with electromagnetic tracking systems is their limited tracking accuracy within their tracking volumes. As a radial distance between an electromagnetic sensor and a field generator increases, the accuracy and precision of tracking that electromagnetic sensor degrades. There is, therefore a need for a system and method for electromagnetic navigation during a dental implant surgery that may allow for maintaining an electromagnetic sensor mounted on a surgical tool or within an oral cavity of a patient at a predetermined distance from a given field generator to ensure the maximum accuracy of tracking that electromagnetic sensor.

Moreover, the presence of any magnetic or ferromagnetic object within an operating environment of an electromagnetic tracking system that may generate or perturb magnetic fields may cause measurement bias and may consequently result in tracking errors ranging from a few millimeters in research environments to a few centimeters in clinical settings. There is, therefore, a further need for a system and method for reducing noise in electromagnetic navigation systems that may allow for performing an accurate and precise tracking of a surgical tool during dental implant surgery in spite of the presence of such objects in an operating environment.

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description and the drawings.

According to one or more exemplary embodiments, the present disclosure is directed to a system for electromagnetic navigation in dental implant placement. An exemplary system may include an electromagnetic tracking system that may be configured to track positions and orientations of a plurality of electromagnetic sensors within a tracking volume. An exemplary tracking volume may encompass a headrest of a dental unit. An exemplary electromagnetic tracking system may include a field generator.

In an exemplary embodiment, an exemplary system electromagnetic navigation in dental implant placement may further include a passive articulating arm that may be attached to an exemplary dental unit from a first end of the passive articulating arm. An exemplary system may further include a parallel manipulator that may include a first plate that may be coupled with a second end of the passive articulating arm, a second plate, where an exemplary field generator may be mounted on the second plate and may be moveable with the second plate, and six prismatic actuators that may be connected between the first plate and the second plate. Each prismatic actuator of the six prismatic actuators may be connected between the first plate and the second plate utilizing two universal joints at either end of each prismatic actuator. The six prismatic actuators may be configured to move the second plate relative to the first plate with six degrees of freedom. An exemplary system may further include a control unit that may be coupled with the parallel manipulator and the electromagnetic tracking system. The control unit may be configured to receive the tracked positions of the plurality of the electromagnetic sensors from the electromagnetic tracking system and to adjust at least a position or an angular orientation of the field generator.

In an exemplary embodiment, the control unit may include a processor, and a memory that may be configured to store executable instructions to cause the processor to receive coordinates of a volume of interest within the tracking volume with respect to the field generator, receive the tracked positions of the plurality of the electromagnetic sensors, and urge the parallel manipulator to adjust at least one of the position and the orientation of the field generator based on the tracked positions of the plurality of the electromagnetic sensors, such that the volume of interest encompasses the tracked positions of the plurality of the electromagnetic sensors at any given instant.

In an exemplary embodiment, the passive articulating arm may include a first arm segment, a second arm segment that may be coupled with the first arm segment utilizing an elbow joint. The second arm and the first arm may be rotatable relative to each other around a single axis of the elbow joint. The passive articulating arm may further include a proximal ball joint that may couple the first arm segment with the dental unit. The first arm segment may be rotatable around the proximal ball joint relative to the dental unit with three rotational degrees of freedom, and a distal ball joint that may couple the second arm segment with the first plate. The first plate may be rotatable around the distal ball joint relative to the second arm segment with three rotational degrees of freedom.

In an exemplary embodiment, the passive articulating arm may be configured to adjust at least one of a position or an angular orientation of the first plate relative to the headrest. In an exemplary embodiment, the proximal ball joint may include a proximal ball stud disposed within a proximal socket attached to the first arm segment. The proximal ball stud may be attached to the headrest.

In an exemplary embodiment, the distal ball stud comprises a distal ball stud may be disposed within a distal socket attached to the second arm segment. The distal ball stud may be attached to the first plate.

In an exemplary embodiment, the plurality of electromagnetic sensors may include a first electromagnetic sensor that may be mounted in an oral cavity of a patient, and a second electromagnetic sensor mounted on a dental handpiece.

In an exemplary embodiment, each prismatic actuator of the six prismatic actuators may include an electric prismatic linear actuator. In an exemplary embodiment, tracked positions of an electromagnetic sensor of the plurality of electromagnetic sensors within the tracking volume may be associated with tracking errors. The volume of interest within the tracking volume may correspond to a region of the tracking volume with the tracking errors less than a predetermined threshold.

In an exemplary embodiment, the tracking errors may include straight-line distances between tracked positions of an electromagnetic sensor of the plurality of the electromagnetic sensors and corresponding exact positions of the electromagnetic sensor within the tracking volume. In an exemplary embodiment, the predetermined threshold may be at most 1 mm. In an exemplary embodiment, the predetermined threshold may be between 0.5 mm and 0.7 mm.

According to one or more exemplary embodiments, the present disclosure is directed to a method for electromagnetic navigation in dental implant placement. An exemplary method may include determining a first volume of interest within a tracking volume of a magnetic tracking system, where the magnetic tracking system may include a field generator and the first volume of interest may be associated with the field generator, tracking a position of an electromagnetic sensor within a tracking volume utilizing the magnetic tracking system, and changing the first volume of interest to a second volume of interest by changing at least one of a position or an orientation of the field generator responsive to the tracked position of the electromagnetic sensor falling outside the first volume of interest, such that the tracked position of the electromagnetic sensor falling within the second volume of interest.

In an exemplary embodiment, determining a first volume of interest within a tracking volume of a magnetic tracking system may include determining a region of the tracking volume wherein tracking errors associated with tracked positions of the electromagnetic sensor are less than a predetermined threshold.

In an exemplary embodiment, determining a region of the tracking volume wherein tracking errors associated with tracked positions of the electromagnetic sensor are less than a predetermined threshold may include determining the tracking errors by calculating straight-line distances between the tracked positions and corresponding exact positions of the electromagnetic sensor within the tracking volume.

In an exemplary embodiment, determining a region of the tracking volume may include determining a region wherein tracking errors associated with tracked positions of the electromagnetic sensor are at most 1 mm.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

Figure 1:
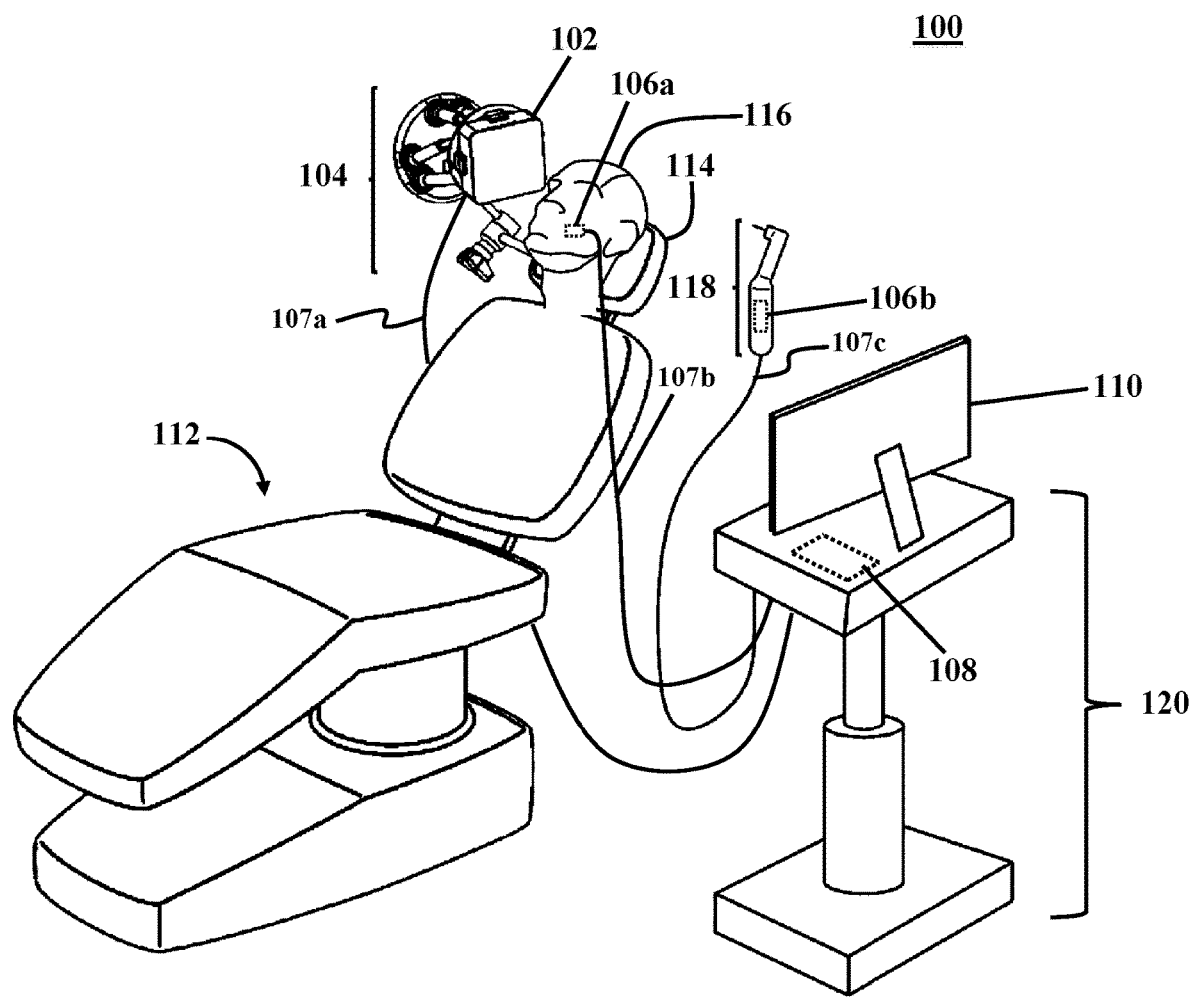
FIG. 1 illustrates a perspective view of an electromagnetic navigation system for dental implant placement, consistent with one or more exemplary embodiments of the present disclosure.

In the following detailed description, numerous specific details are set forth by way of examples to provide a thorough understanding of the relevant teachings related to the exemplary embodiments. However, it should be apparent that the present teachings may be practiced without such details. In other instances, well-known methods, procedures, components, or circuitry have been described at a relatively high-level, without detail, in order to avoid unnecessarily obscuring aspects of the present teachings.

The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be plain to one skilled in the art, and the general principles defined herein may be applied to other implementations and applications without departing from the scope of the present disclosure. The present disclosure is not intended to be limited to the implementations shown but is to be accorded the broadest possible scope consistent with the principles and features disclosed herein.

The present disclosure is directed to exemplary systems and exemplary methods for robust electromagnetic navigation in dental implant surgery. An exemplary electromagnetic navigation system may include a field generator, at least one electromagnetic sensor, and a control unit. An exemplary field generator may be utilized for generating a magnetic field through a tracking volume at a site of surgery. A magnetic field generated by an exemplary field generator may allow for localizing and tracking exemplary electromagnetic sensors mounted on surgical tools and exemplary electromagnetic sensors inside an oral cavity of a patient within the generated magnetic field.

An exemplary electromagnetic navigation system may determine position and orientation of an exemplary electromagnetic sensor by measuring the behavior of the exemplary electromagnetic sensor within an exemplary electromagnetic field generated by an exemplary field generator. A current may be induced in an exemplary electromagnetic sensor that may be a function of the position and orientation of the exemplary electromagnetic sensor relative to an exemplary field generator.

However, an exemplary magnetic field generated by an exemplary field generator may vary over a tracking volume around the exemplary field generator, such that the accuracy of an exemplary electromagnetic navigation system may be spatially dependent. A tracking volume around an exemplary field generator may include a region of maximum accuracy at a certain distance from the exemplary field generator. Beyond a region of maximum accuracy of a tracking volume, tracking accuracy may decrease as the distance between an exemplary electromagnetic sensor and an exemplary field generator increases. In order to achieve the maximum possible accuracy in determining the position and orientation of an exemplary electromagnetic sensor, the exemplary electromagnetic sensor and an exemplary surgical site must be within a region of maximum accuracy of a tracking volume.

In dental implant surgery, an exemplary electromagnetic sensor may be placed inside a surgical tool, such as a drill, and may be moved through a surgical site. As used herein, an exemplary surgical site may refer to a volume of interest around a portion of a patient's jawbone into which a dental implant is to be inserted. An exemplary electromagnetic navigation system may be configured to track the position and orientation of the surgical tool by tracking the position and orientation of the exemplary electromagnetic sensor during dental implant surgery.

In common practice, magnetic field generators are positioned manually close to a predetermined surgical site and the position and orientation of the magnetic field generators are not usually changed during surgery. Therefore, during surgery, it may be possible that the predetermined surgical site or a surgical tool may fall outside a region of maximum accuracy within the tracking volume, which may adversely affect the precision of the electromagnetic tracking system. According to one or more exemplary embodiments of the present disclosure, an exemplary electromagnetic navigation system maybe configured to adjust the position and orientation of an exemplary field generator with respect to a predetermined surgical site and a surgical tool to ensure placement of the predetermined surgical site and the surgical tool within a region of maximum accuracy of an exemplary tracking volume of the exemplary magnetic field generator.

Another source of disturbance or noise that may affect the accuracy and precision of an exemplary electromagnetic navigation system may be a surgical tool itself. Materials used in a surgical tool may be of magnetic or ferromagnetic nature and may reduce the accuracy of the surgical tool tracking by affecting the electromagnetic field generated by an exemplary electromagnetic field generator. Moreover, when an exemplary surgical tool, such as a drill is turned on during surgery, an electric actuator that drives the drill may create a noise that may further reduce the accuracy of the surgical tool tracking.

According to one or more exemplary embodiments of the present disclosure, in an exemplary electromagnetic navigation system, a mounting location of an exemplary electromagnetic sensor on an exemplary surgical tool may be calibrated such that the exemplary sensor may be placed at a location on the exemplary surgical tool where interference of an actuator of the exemplary surgical tool may be at its minimum. In addition, an exemplary control unit of an exemplary electromagnetic navigation system may further include a frequency filter that may be activated when an exemplary surgical tool is turned on during surgery. An exemplary frequency filter may filter out noises created due to activation of an exemplary electric actuator of an exemplary surgical tool.

FIG. 1 illustrates a perspective view of an electromagnetic navigation system 100 for dental implant placement, consistent with one or more exemplary embodiments of the present disclosure. In an exemplary embodiment, electromagnetic navigation system 100 may include a field generator 102 configured to generate an electromagnetic field, a positioning arm 104 that may be utilized for mounting field generator 102 to a headrest 114 of a dental unit 112. In an exemplary embodiment, electromagnetic navigation system 100 may further include a first electromagnetic sensor 106a attachable to a patient's head 116 and a second electromagnetic sensor 106b attachable to a handpiece 118.

In an exemplary embodiment, first electromagnetic sensor 106a may be attached within an oral cavity of a patient, for example, on a tooth, gum, or jawbone of a patient. In an exemplary embodiment, electromagnetic navigation system 100 may be configured to track movements of patient's head 116 by tracking the position and orientation of first electromagnetic sensor 106a relative to field generator 102.

In an exemplary embodiment, second electromagnetic sensor 106b may be attached to handpiece 118. As used herein, handpiece 118 may refer to any of a variety of specially adapted dental surgical instruments, such as dental drills. In an exemplary embodiment, electromagnetic navigation system 100 may be configured for tracking movements of handpiece 118 by tracking the position and orientation of second electromagnetic sensor 106b relative to field generator 102.

In an exemplary embodiment, electromagnetic navigation system 100 may further include a control unit 108 that may be connected to filed generator 102, first electromagnetic sensor 106a, and second electromagnetic sensor 106b via communication lines 107a, 107b, and 107c, respectively. In an exemplary embodiment, control unit 108 may be configured to monitor movements of handpiece 118 and movements of patient's head 116 with respect to field generator 102. In an exemplary embodiment, control unit 108 may further be configured to map movements of handpiece 118 on a pre-recorded CBCT volume of a patient's oral cavity and to display a precise location of handpiece 118 on the pre-recorded CBCT volume on a monitor 110. In an exemplary embodiment, control unit 108 and monitor 110 may be mounted on a surgical trolley or stand 120 near dental unit 112, and a surgeon may have available on monitor 110, a CBCT volume of a patient's oral cavity associated with a precise location of handpiece 118 during the dental implant placement procedure.

Figure 2:
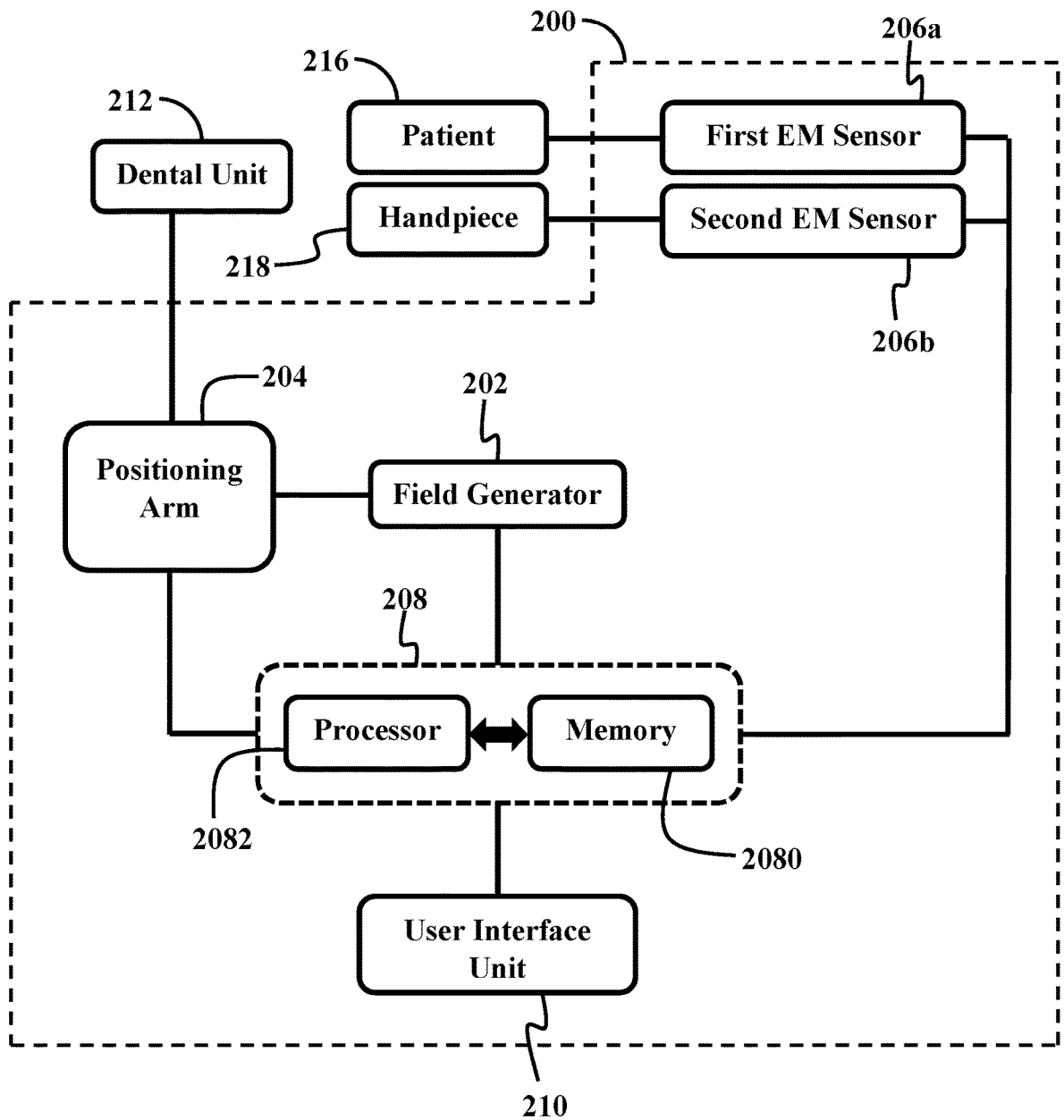
FIG. 2 illustrates a block diagram of an electromagnetic navigation system for dental implant placement, consistent with one or more exemplary embodiments of the present disclosure.

FIG. 2 illustrates a block diagram of an electromagnetic navigation system 200 for dental implant placement, consistent with one or more exemplary embodiments of the present disclosure. In an exemplary embodiment, electromagnetic navigation system 200 may be similar to electromagnetic navigation system 100.

In an exemplary embodiment, electromagnetic navigation system 200 may include a field generator 202 similar to field generator 102, a positioning arm 204 similar to positioning arm 104 coupled to a dental unit 212 similar to dental unit 112, a first electromagnetic sensor 206a similar to first electromagnetic sensor 106a, a second electromagnetic sensor 206b similar to second electromagnetic sensor 106b, and a control unit 208 similar to control unit 108.

In an exemplary embodiment, first electromagnetic sensor 206a may be attached within an oral cavity of a patient 216, for example on a tooth, gum, or jawbone of patient 216. In an exemplary embodiment, electromagnetic navigation system 200 may be configured to track movements of a head of patient 216 similar to patient's head 116 by tracking the position and orientation of first electromagnetic sensor 206a relative to field generator 202.

In an exemplary embodiment, second electromagnetic sensor 206b may be attached to a handpiece 218 similar to handpiece 118. In an exemplary embodiment, electromagnetic navigation system 200 may be configured to track movements of handpiece 218 by tracking the position and orientation of second electromagnetic sensor 206b relative to field generator 202.

In an exemplary embodiment, control unit 208 may be a programmable logic controller such as a personal computer that may include a memory 2080 and a processor 2082. Memory 2080 may include executable instructions that, when executed, may cause processor 2082 to perform operations that in an exemplary embodiment may include processing received signals from first electromagnetic sensor 206a and second electromagnetic sensor 206b to track positions and orientations of first electromagnetic sensor 206a and second electromagnetic sensor 206b relative to field generator 202.

In an exemplary embodiment, memory 2080 may further store sets of pre-recorded images that may be obtained by a CT or CBCT scanner before dental implant placement procedure. In an exemplary embodiment, a patient's oral and maxillofacial area may be scanned by a CBCT scanner to obtain a volumetric data set. An exemplary scanning software may then collect the volumetric data and may reconstruct it to produce a CBCT volume. In an exemplary embodiment, memory 2080 may store a CBCT volume that may include a patient's surgical anatomy of interest, for example, an entire mandible or an entire maxilla of patient 216.

In an exemplary embodiment, memory 2080 may further store executable instructions that, when executed, cause processor 2082 to determine a transform that may relate tracked positions and orientations of first electromagnetic sensor 206a and second electromagnetic sensor 206b to the CBCT volume stored in memory 2080. In an exemplary embodiment, memory 2080 may further store executable instructions that, when executed, cause processor 2082 to utilize the determined transform to map tracked positions and orientations of first electromagnetic sensor 206a and second electromagnetic sensor 206b to the stored CBCT volume.

In exemplary embodiments, electromagnetic navigation system 200 may further include a user interface unit 210 that may be coupled in data communication to control unit 208 via wired links, wireless links, or a combination of wired and wireless links. In an exemplary embodiment, user interface unit 210 may include a monitor or display similar to monitor 110. In exemplary embodiments, mapping tracked positions and orientations of first electromagnetic sensor 206a and second electromagnetic sensor 206b to the CBCT volume may allow for mapping positions and orientations of handpiece 218 onto the stored CBCT volume. After that, as a surgeon moves handpiece 218 within a surgical site, images may appear on a monitor or display of user interface unit 210 responsive to the tracked positions and orientations of handpiece 218. In an exemplary embodiment, the images appearing on the monitor or display of user interface unit 210 may include a graphic representation of handpiece 218 mapped over the CBCT volume.

As discussed, magnetic fields that may be generated by field generator 202 may vary over a tracking volume around field generator 202, such that the accuracy of electromagnetic navigation system 200 may be spatially dependent. The tracking volume around field generator 202 may include a region of maximum accuracy. Beyond the region of maximum accuracy of the tracking volume, tracking accuracy may decrease as the distance between field generator 202 and first electromagnetic sensor 206a and second electromagnetic sensor 206b increases. In exemplary embodiments, in order to achieve the maximum possible accuracy in determining the position and orientation of first electromagnetic sensor 206a and second electromagnetic sensor 206b, first electromagnetic sensor 206a and second electromagnetic sensor 206b and an exemplary surgical site must be within the region of maximum accuracy of the tracking volume.

Accordingly, in an exemplary embodiment, memory 2080 may further include executable instructions that, when executed, cause processor 2082 to perform operations that in an exemplary embodiment may include determining a region of maximum accuracy with a tacking volume of field generator 202 and continuously adjusting position and orientation of field generator 202 during dental implant placement to maintain first electromagnetic sensor 206a and second electromagnetic sensor 206b within the region of maximum accuracy.

In an exemplary embodiment, control unit 208 may further be functionally coupled to positioning arm 204 via wired links, wireless links, or a combination of wired and wireless links. In an exemplary embodiment, field generator 202 may be attached to dental unit 212 via positioning arm 204. In an exemplary embodiment, adjusting position and orientation of field generator 202 may include urging positioning arm 204 utilizing processor 2082 to change the position and orientation of field generator 202 to maintain first electromagnetic sensor 206a and second electromagnetic sensor 206b within the region of maximum accuracy.

Figure 3A:
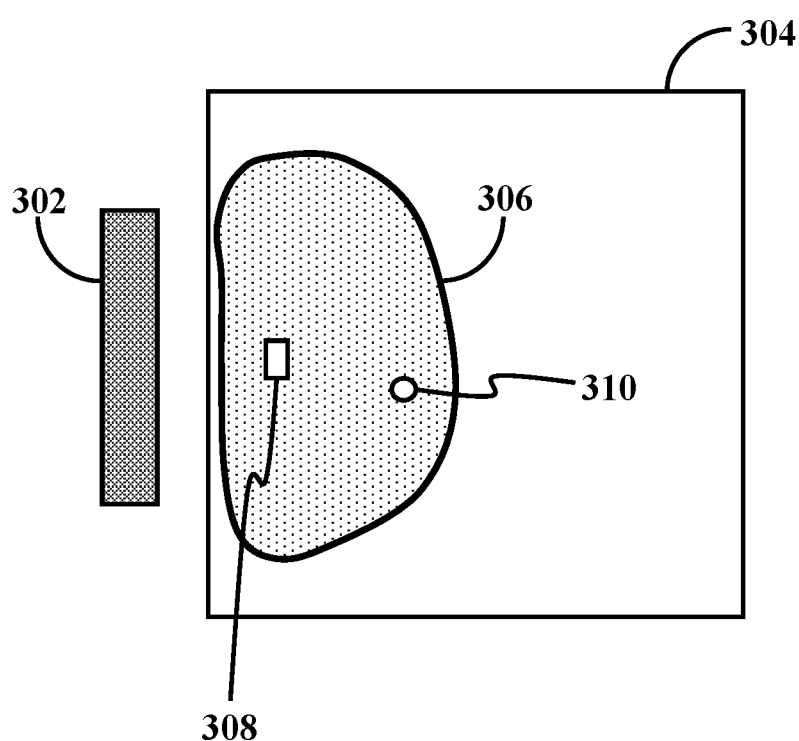
FIGS. 3A-3C illustrate schematic views of a region of maximum accuracy of a tracking volume of a field generator, consistent with one or more exemplary embodiments of the present disclosure.
Figure 3B:
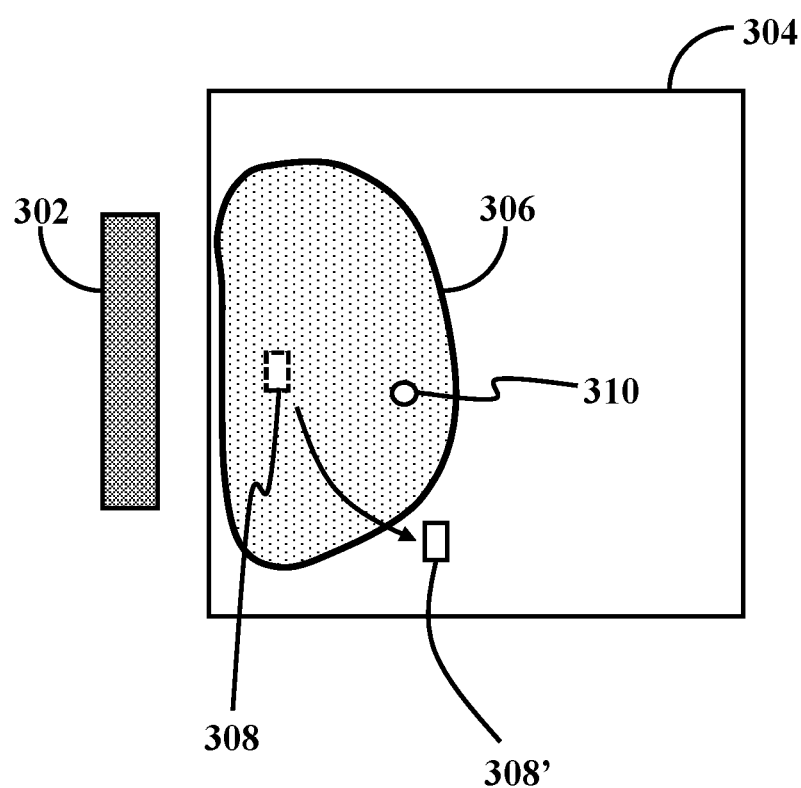
Figure 3C:
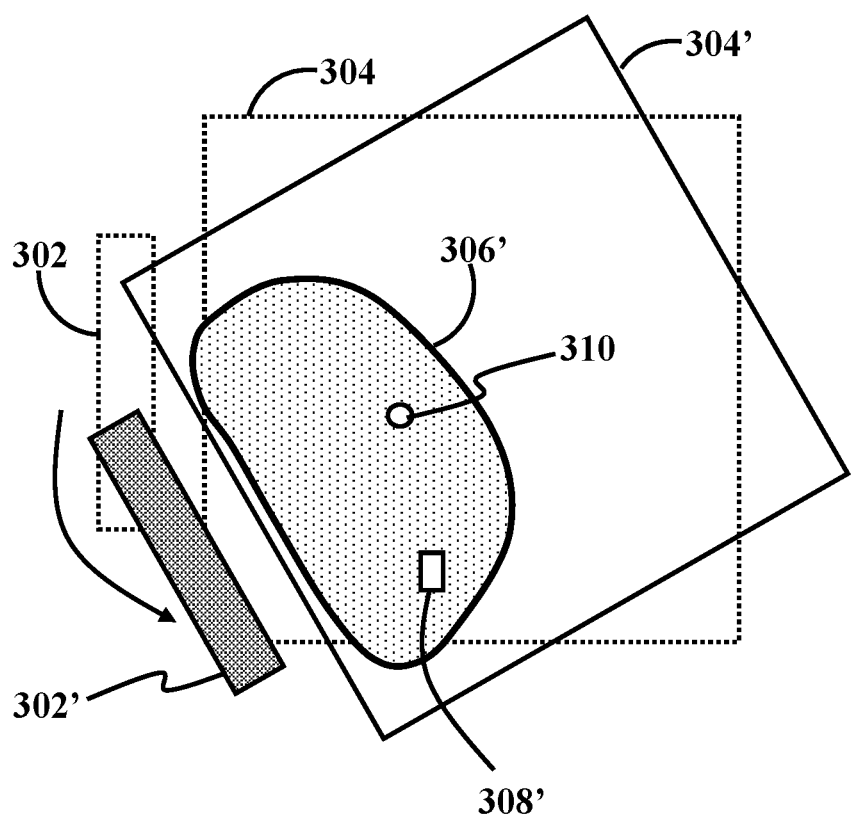

FIGS. 3A-3C illustrate schematic views of a region of maximum accuracy 306 of a tracking volume 304 of a field generator 302, consistent with one or more exemplary embodiments of the present disclosure. In an exemplary embodiment, field generator 302 may provide a tracking volume 304 around a surgical site, within which positions and orientations of a patient's reference sensor and a handpiece reference sensor may be tracked. In an exemplary embodiment, tracking volume 304 may refer to a volume, through which field generator 302 generates an electromagnetic field. In an exemplary embodiment, the patient's reference sensor may be similar to first electromagnetic sensor 206a, and the handpiece reference sensor may be similar to second electromagnetic sensor 206b.

In an exemplary embodiment, a tracked position of an exemplary handpiece reference is designated by rectangle 308, and a tracked position of an exemplary patient's reference is designated by circle 310 in FIGS. 3A-3C. As mentioned before, an exemplary electromagnetic navigation system, such as electromagnetic navigation system 200, may be configured to continuously adjust position and orientation of an exemplary field generator, such as field generator 302, during dental implant placement to maintain an exemplary patient's reference and an exemplary handpiece reference within region of maximum accuracy 306. For example, if a surgeon moves an exemplary handpiece from a first position within region of maximum accuracy 306 as shown by rectangle 308 to a second position outside region of maximum accuracy 306 as shown by rectangle 308' in FIG. 3B, electromagnetic navigation system 200 may move field generator 302 to a second position designated by reference numeral 302' as shown in FIG. 3C to keep both the patient's reference and the handpiece reference within a now moved region of maximum accuracy 306'. In exemplary embodiments, moving field generator 302 to the second position and orientation designated by reference numeral 302' may lead to tracking volume 304 to change into a new tracking volume 304' and region of maximum accuracy 306 to change into a new region designated by reference numeral 306'. In exemplary embodiments, a location of region of maximum accuracy 306 with respect to position and orientation of field generator 302 may be a constant and may be determined by calibration, as will be discussed below.

In an exemplary embodiment, region of maximum accuracy 306 of tracking volume 304 around a given surgical site may be determined by calibrating a magnetic navigation system such as electromagnetic navigation system 200. In an exemplary embodiment, calibrating an exemplary magnetic navigation system may include determining tracking errors throughout an entire area or a portion of interest of tracking volume 304 and identifying a region within tracking volume 304 as a region of maximum accuracy, where tracking errors are less than a predetermined threshold. In an exemplary embodiment, the predetermined threshold may be at most 1 mm. In an exemplary embodiment, the predetermined threshold may be between 0.5 mm and 0.7 mm. Further details about calibrating are provided below with respect to FIGS. 4A-C.

Figure 4A:
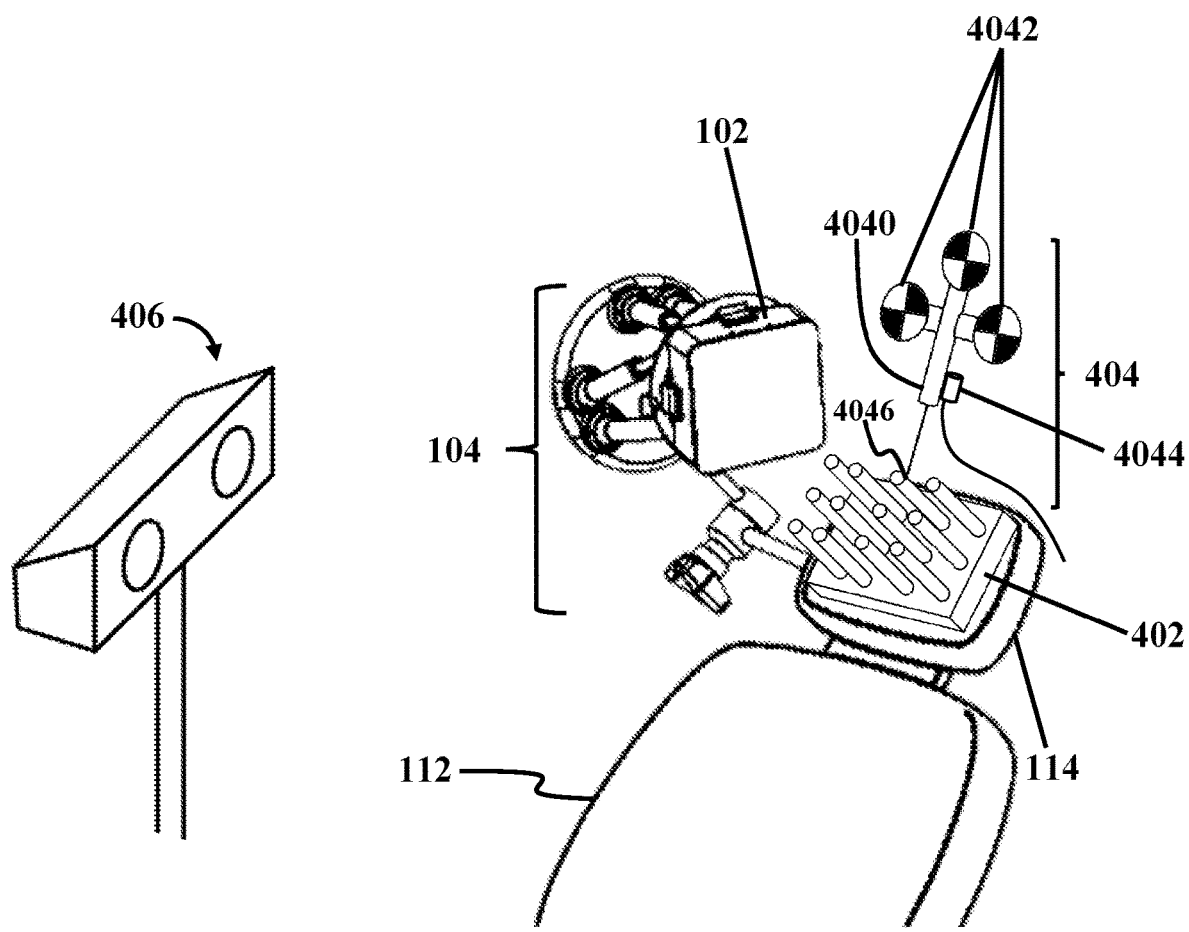
FIG. 4A illustrates a perspective view of a calibration setup for calibrating an electromagnetic navigation system, consistent with one or more exemplary embodiments of the present disclosure.

FIG. 4A illustrates a perspective view of a calibration setup for calibrating an electromagnetic navigation system, consistent with one or more exemplary embodiments of the present disclosure. In an exemplary embodiment, a region of maximum accuracy for an exemplary electromagnetic navigation system may be identified by calibrating the exemplary electromagnetic navigation system in a region of interest. In an exemplary embodiment, a region of interest in dental implant surgery may be a region surrounding the surgical site, which is a region surrounding an oral cavity of a patient.

In an exemplary embodiment, before an exemplary dental implant placement procedure, an exemplary electromagnetic navigation system, such as electromagnetic navigation system 100 may be calibrated to find a region of maximum accuracy. In an exemplary embodiment, after an exemplary field generator such as field generator 102 is coupled to an exemplary headrest such as headrest 114 of dental unit 112, a calibration phantom 402 may be placed over headrest 114. Since in dental implant surgery, a surgical site is defined as an area surrounding an oral cavity of a patient, calibration phantom 402 may be positioned on headrest 114 where an oral cavity of a patient is located during surgery. In an exemplary embodiment, calibration phantom 402 may include a plurality of points with known true positions.

In an exemplary embodiment, an error indicating tool 404 may be utilized for determining tracking errors throughout an entire area or a portion of a tracking volume defined by calibration phantom 402. In an exemplary embodiment, error indicating tool 404 may include a probe 4040, on which optical markers 4042 and an electromagnetic sensor 4044 may be mounted. In an exemplary embodiment, relative mounting positions of optical markers 4042 and electromagnetic sensor 4044 on probe 4040 may be a known constant, such that by tracking optical markers 4042 or electromagnetic sensor 4044, a tip 4046 of probe 4040 may be tracked. In an exemplary embodiment, an optical camera 406 may be utilized for tracking optical markers 4042.

Figure 4B:
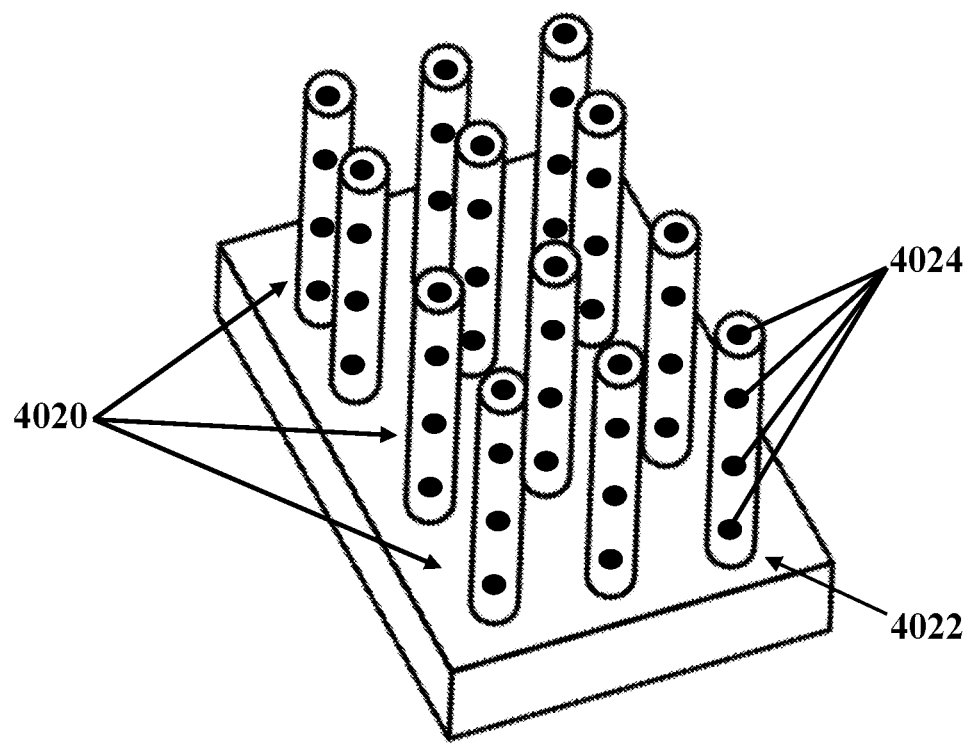
FIG. 4B illustrates a perspective view of a calibration phantom, consistent with one or more exemplary embodiments of the present disclosure.

FIG. 4B illustrates a perspective view of calibration phantom 402, consistent with one or more exemplary embodiments of the present disclosure. In an exemplary embodiment, calibration phantom 402 may include a plurality of vertically arranged bars 4020. In an exemplary embodiment, each bar of plurality of vertically arranged bars 4020, for example, bar 4022 may include a plurality of tracking points 4024 that together with tracking points of other vertically arranged bars may form a three-dimensional matrix of tracking points. In an exemplary embodiments, true positions of the plurality of tracking points are known relative to each other. It should be understood that calibration phantom 402 may provide an exemplary three-dimensional matrix of tracking points with any other possible structure and by no means is limited to the structure illustrated in FIG. 4B.

In an exemplary embodiment, a calibration process may include placing tip 4046 of error indicating tool 404 over each tracking point on calibration phantom 402 and then utilizing optical markers 4042 and electromagnetic sensor 4044 to track the position of tip 4046. In an exemplary embodiment, for each tracking point on phantom 402, a true position of a tracking point may be determined by tracking tip 4046 utilizing optical markers 4042 and a tracked position of a tracking point may be determined by tracking tip 4046 utilizing electromagnetic sensor 4044. In an exemplary embodiment, a tracking error for each tracking point on phantom 402 may be obtained by finding a straight line distance between the true position of each tracking point and the tracked position of each tracking point. In an exemplary embodiment, in order to identify a region of maximum accuracy, a map of all tracking errors obtained for all tracking points on phantom 402 may be determined by the above-described calibration process and a region of the determined map, in which tracking errors are less than a predetermined threshold may be identified as a region of maximum accuracy. In exemplary embodiments, an exemplary electromagnetic navigation system, such as electromagnetic navigation system 100 or 200 may be configured to maintain a handpiece reference sensor and a patient's reference sensor within an identified region of maximum accuracy as was discussed in preceding sections.

Figure 5A:
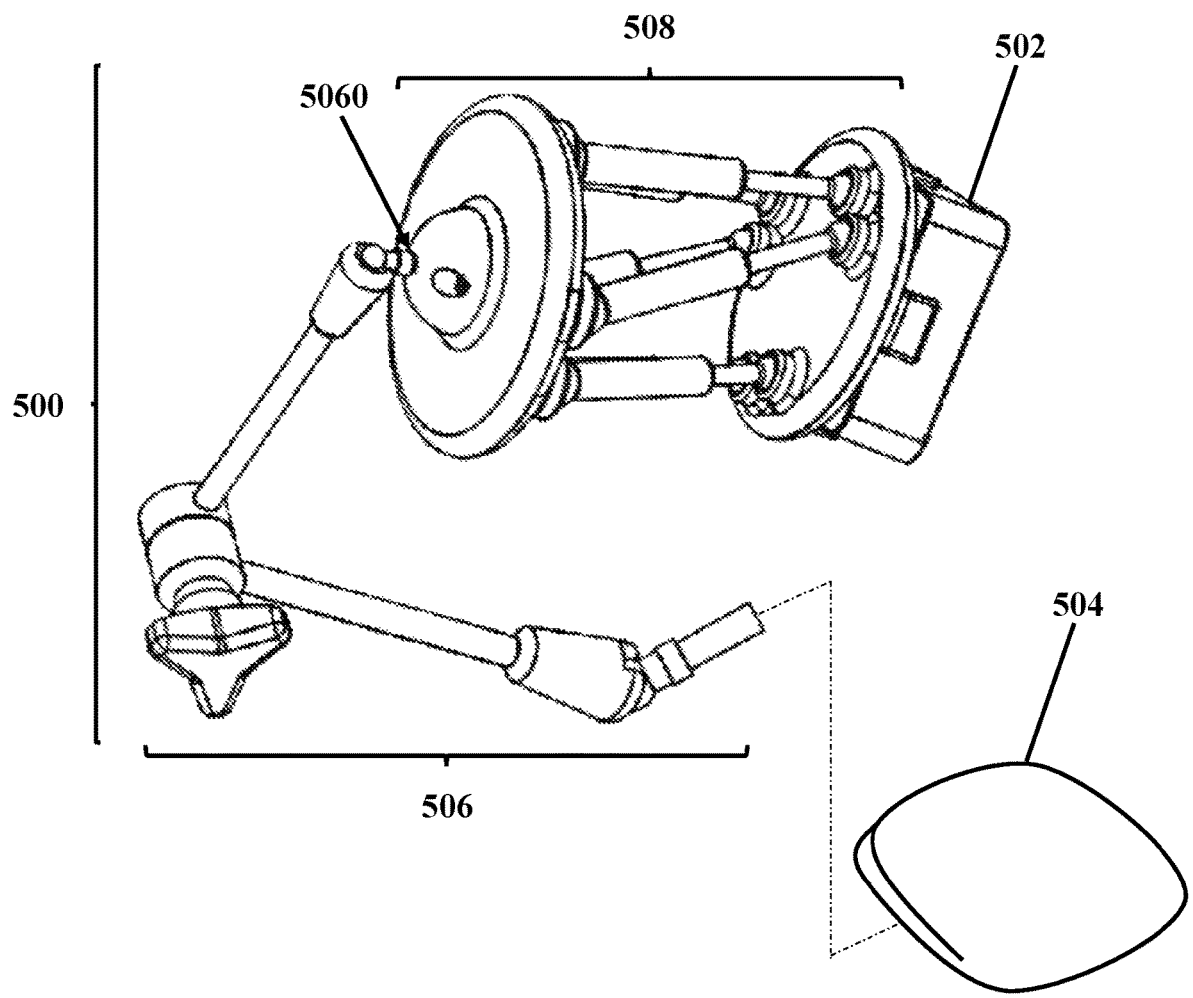
FIG. 5A illustrates a perspective view of a positioning arm, consistent with one or more exemplary embodiments of the present disclosure.

FIG. 5A illustrates a perspective view of a positioning arm 500, consistent with one or more exemplary embodiments of the present disclosure. In an exemplary embodiment, positioning arm 500 may be similar to positioning arm 204 and may be utilized for adjusting the position and orientation of a field generator 502 similar to field generator 202. In an exemplary embodiment, field generator 502 may be attached to a headrest 504 of a dental unit utilizing positioning arm 500. In an exemplary embodiment, positioning arm 500 may include a passive articulating arm 506 and an active parallel manipulator 508 coupled to a distal end 5060 of articulating arm 506.

Figure 5B:
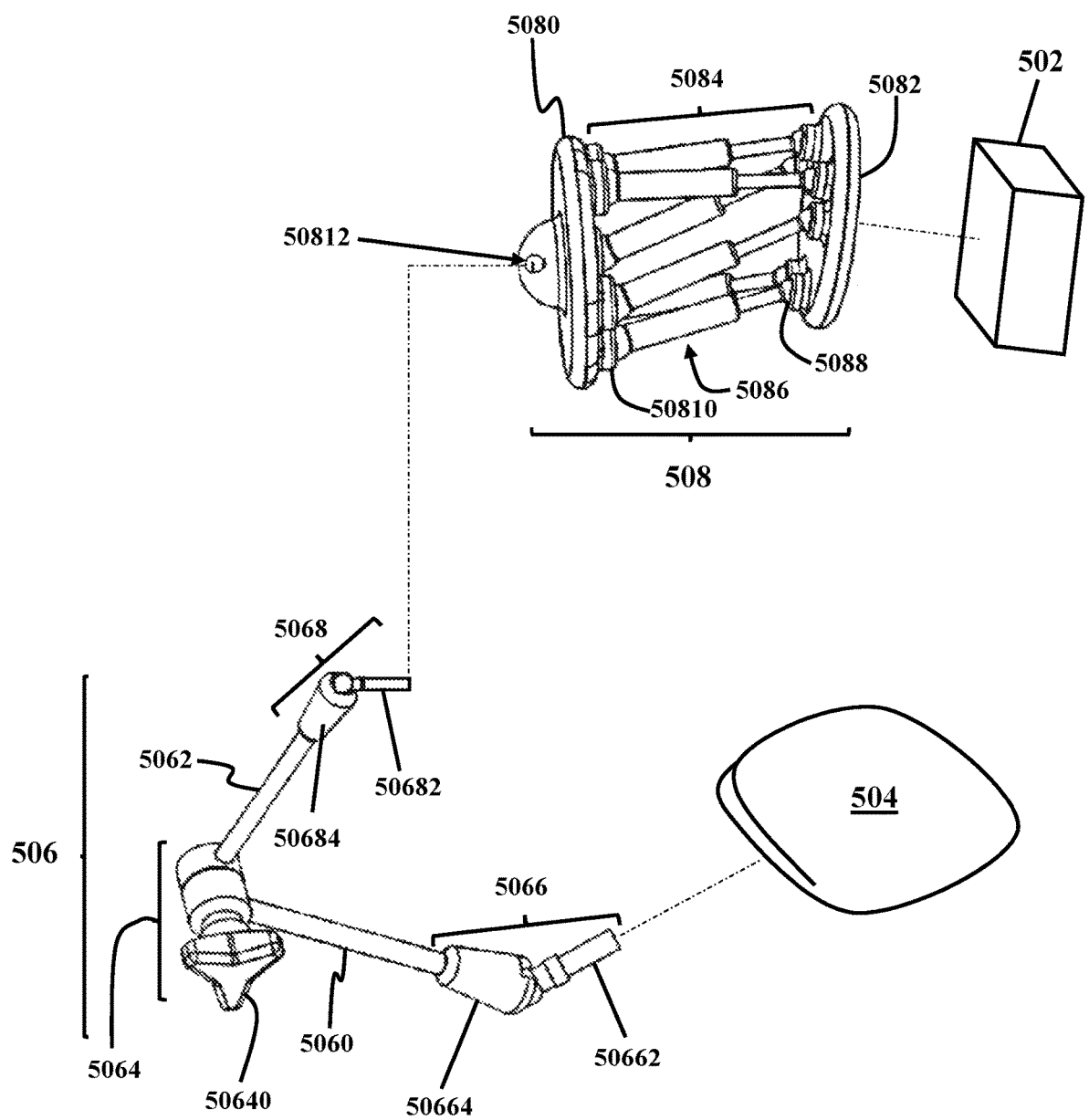
FIG. 5B illustrates an exploded view of a positioning arm, consistent with one or more exemplary embodiments of the present disclosure.

FIG. 5B illustrates an exploded view of positioning arm 500, consistent with one or more exemplary embodiments of the present disclosure. In an exemplary embodiment, passive articulating arm 506 may include a first arm segment 5060 and a second arm segment 5062 that may be joined together utilizing an elbow joint 5064. In an exemplary embodiment, elbow joint 5064 may provide a common axis between first arm segment 5060 and second arm segment 5062, around which first arm segment 5060 and second arm segment 5062 may be rotated relative to each other. In an exemplary embodiment, elbow joint 5064 may be equipped with a locking knob 50640 that may be utilized to lock elbow joint 5064 at a desired angle between first arm segment 5060 and second arm segment 5062.

In an exemplary embodiment, articulating arm 506 may further include a proximal ball joint 5066 that may be attached to first arm segment 5060 and a distal ball joint 5068 that may be attached to second arm segment 5062. In an exemplary embodiment, proximal ball joint 5066 may be utilized for connecting articulating arm 506 to headrest 504, and distal ball joint 5068 may be utilized for connecting articulating arm 506 to active parallel manipulator 508.

In an exemplary embodiment, proximal ball joint 5066 may include a proximal ball stud 50662 that may be coupled with a proximal socket 50664. In an exemplary embodiment, proximal ball stud 50662 may be a threaded stud that may be utilized for attaching proximal ball joint 5066 to headrest 504, where threaded proximal ball stud 50662 may be screwed into a hole on a rear side of headrest 504.

In an exemplary embodiment, distal ball joint 5068 may include a distal ball stud 50682 that may be coupled with a distal socket 50684. In an exemplary embodiment, distal ball stud 50682 may be a threaded stud that may be utilized for attaching distal ball joint 5068 to active parallel manipulator 508, where threaded distal ball stud 50682 may be screwed into a hole 50812 on active parallel manipulator 508.

In an exemplary embodiment, active parallel manipulator 508 may include a first plate 5080 that may be attached to articulating arm 506, a second plate 5082 that may be utilized for mounting filed generator 502. In an exemplary embodiment, first plate 5080 and second plate 5082 may be interconnected with six prismatic actuators 5084 that may be linear actuators, such as electric linear actuators or hydraulic linear actuators. In an exemplary embodiment, prismatic actuators 5084 may be attached in pairs to three points of attachment on first plate 5080 and may cross over to three points of attachment on second plate 5082. In an exemplary embodiment, each prismatic actuator may be connected between first plate 5080 and second plate 5082 utilizing two universal joints at either end of each prismatic actuator. For example, prismatic actuator 5086 may be connected between first plate 5080 and second plate 5082 utilizing universal joints 5088 and 50810 at either end of prismatic actuator 5086.

In an exemplary embodiment, prismatic actuators 5084 may include electric linear actuators that may be functionally coupled to control unit 208. In an exemplary embodiment, control unit 208 may be configured to adjust the position and orientation of second plate 5082 with respect to first plate 5080 by manipulating an amount of extension or retraction of each pair of prismatic actuators 5084. In exemplary embodiments, such adjustment of the position and orientation of second plate 5082 may allow for adjusting the position and orientation of field generator 502 attached to second plate 5082.

Figure 6:
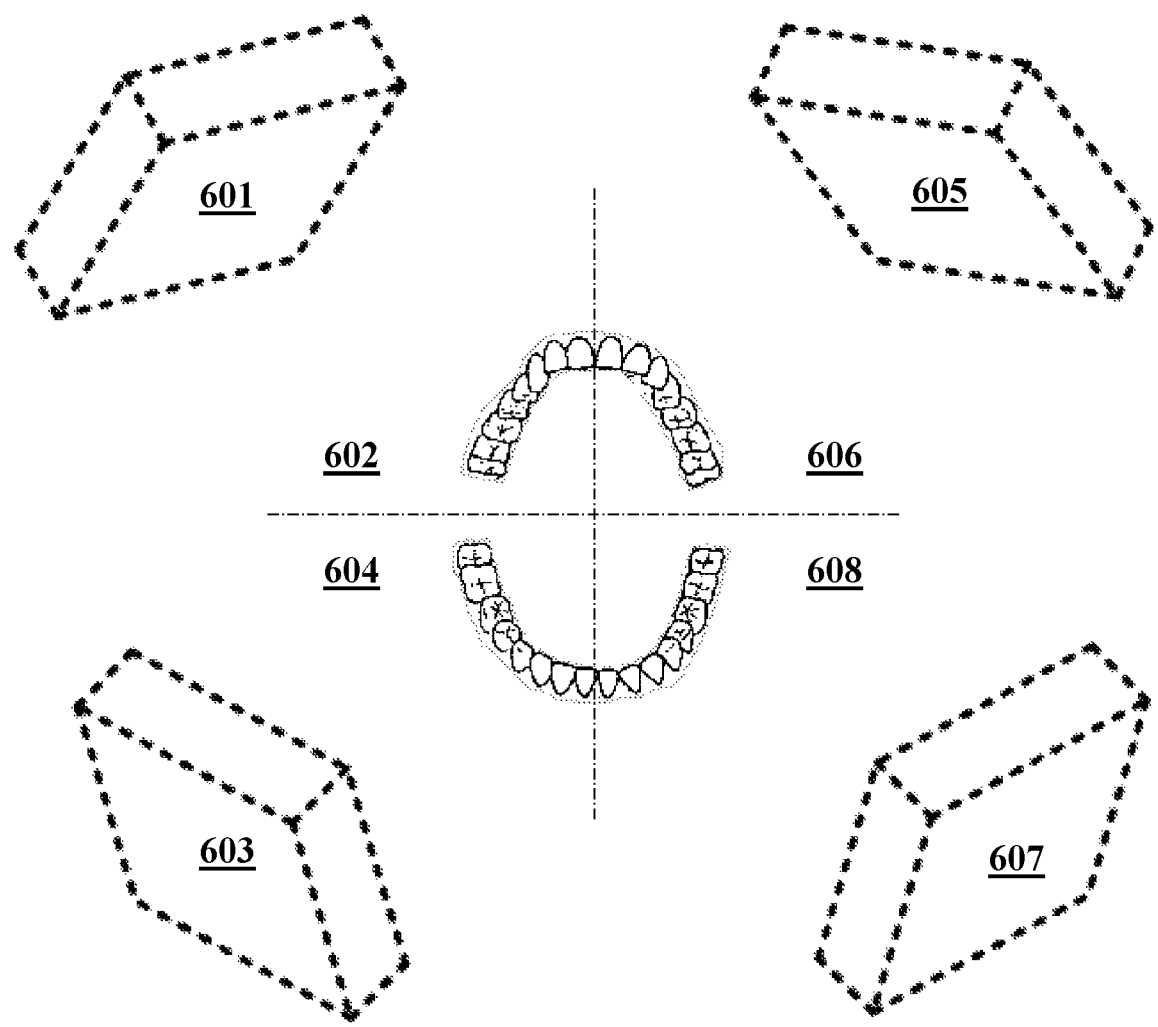
FIG. 6 illustrates a schematic view of possible positions of a field generator with respect to a patient's oral cavity, consistent with one or more exemplary embodiments of the present disclosure.

FIG. 6 illustrates a schematic view of possible positions of a field generator with respect to a patient's oral cavity, consistent with one or more exemplary embodiments of the present disclosure. In an exemplary embodiment, a mounting position of a field generator with respect to a patient's mouth may be determined based at least in part on a location of dental implant placement, i.e., the surgical site. In case a dental implant is to be placed in an upper left quadrant 602 of a patient's mouth, an exemplary field generator may be positioned near upper right quadrant 606 as indicated by box 605. In case a dental implant is to be placed in a lower left quadrant 604 of a patient's mouth, an exemplary field generator may be positioned near lower right quadrant 608 as indicated by box 607. In case a dental implant is to be placed in an upper right quadrant 606 of a patient's mouth, an exemplary field generator may be positioned near upper left quadrant 602 as indicated by box 601. In case a dental implant is to be placed in a lower right quadrant 608 of a patient's mouth, an exemplary field generator may be positioned near lower left quadrant 604 as indicated by box 603.

In an exemplary embodiment, such rough adjustment of the position of an exemplary field generator around a patient's head may be carried out utilizing a passive articulating arm, such as passive articulating arm 506 that may provide a 6 degrees of freedom for adjusting the position of an exemplary field generator at four possible locations as shown by boxes 601, 603, 605, and 607. In exemplary embodiments, first, the position of field generator 502 may be roughly adjusted utilizing passive articulating arm 506 based at least in part on a location of dental implant placement, and then active parallel manipulator 508 may be utilized for fine tuning the position and orientation of field generator 502 as will be discussed.

Figure 7A:
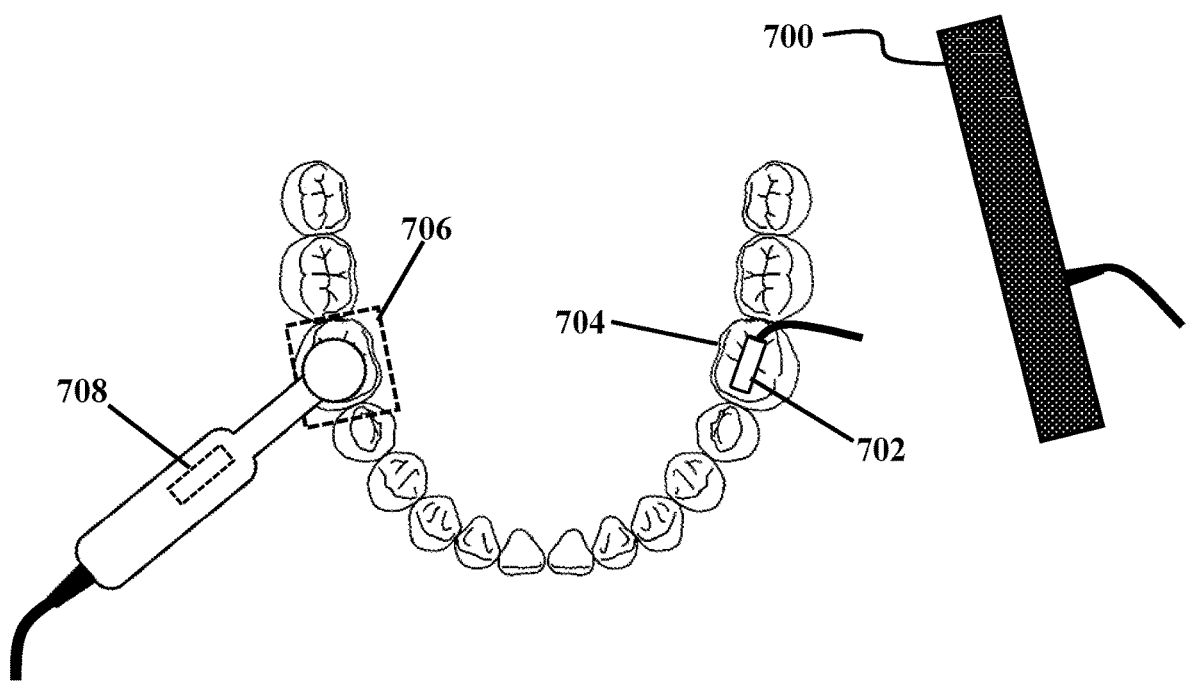
FIGS. 7A-7B illustrate schematic top views of a field generator positioned near a patient's lower teeth, consistent with one or more exemplary embodiments of the present disclosure.
Figure 7B:
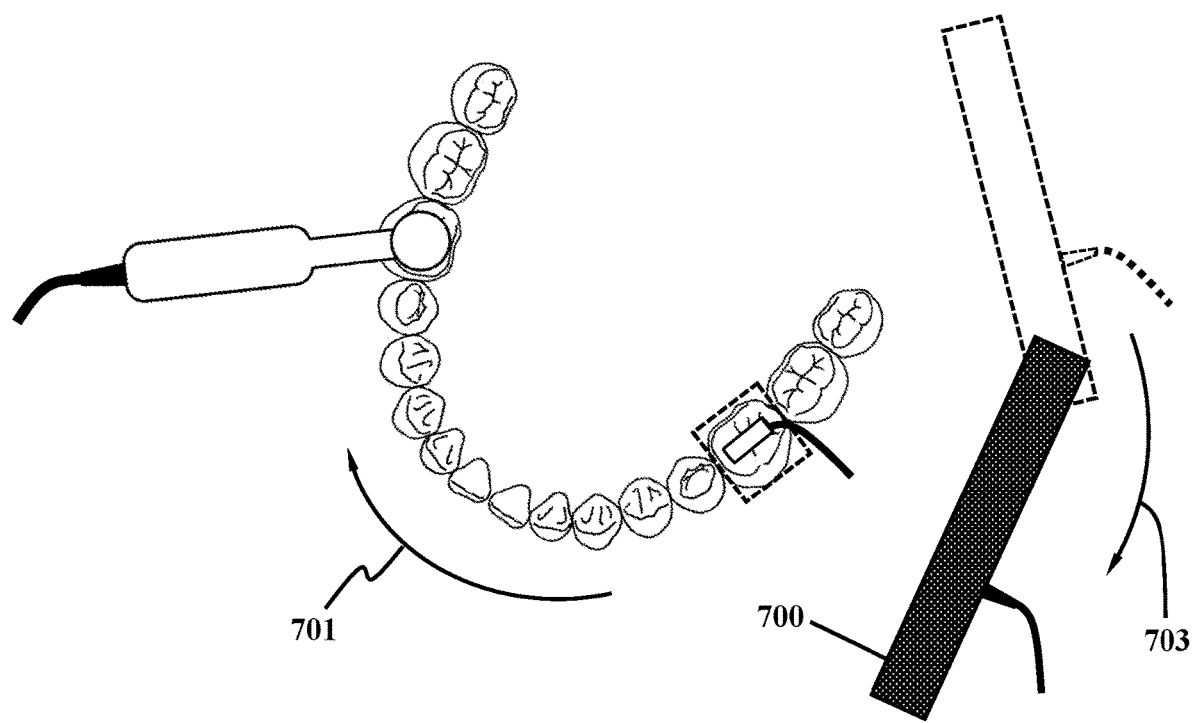

FIGS. 7A and 7B illustrate schematic top views of a field generator 700 positioned near a patient's lower teeth, consistent with one or more exemplary embodiments of the present disclosure. In an exemplary embodiment, a patient's reference sensor may be mounted on a tooth in a quadrant opposite to a quadrant in which a surgical site is located. For example, a patient's reference sensor 702 that may be similar to first electromagnetic sensor 206a may be mounted on tooth 704 of a patient, which is located in a quadrant opposite to the quadrant where surgical site 706 is located. In an exemplary embodiment, patient's reference sensor 702 may either be directly cemented to tooth 704 or indirectly mounted on tooth 704 utilizing a mounting member.

In an exemplary embodiment, field generator 700 may also be roughly positioned at a side of a patient's face opposite to surgical site 706 utilizing degrees of freedom provided by articulating arm 506. In an exemplary embodiment, rough adjustment of field generator 700 utilizing articulating arm 506 may be carried out manually by a user. In an exemplary embodiment, during dental implant placement, magnetic navigation system 200 may track positions and orientations of patient's reference sensor 702 and a handpiece reference sensor 708. In an exemplary embodiment, position and orientation of field generator 700 may further be fine-tuned based on positions and orientations of patient's reference sensor 702 and handpiece reference sensor 708 utilizing active parallel manipulator 508 to keep the positions and orientations of patient's reference sensor 702 and handpiece reference sensor 708 within a region of maximum accuracy of field generator 700. For example, in response to the patient's head rotating in a direction shown by arrow 701, magnetic navigation system 200 may urge field generator 700 to rotate around the patient's head in a direction shown by arrow 703 utilizing active parallel manipulator 508.

As discussed in preceding sections, when an exemplary surgical tool, such as a drill is turned on during surgery, an electric actuator that drives the drill may create a noise or an electromagnetic interference that may further reduce the accuracy of a surgical tool tracking by an exemplary electromagnetic navigation system. In an exemplary embodiment, first, a mounting position of an exemplary electromagnetic sensor on an exemplary handpiece may be calibrated such that the mounting position corresponds to a position of maximum accuracy on the exemplary handpiece. After that, in an exemplary embodiment, an amount of noise created by an exemplary electric actuator of an exemplary handpiece may be determined in order to allow an exemplary navigation system to filter out the noise created by the exemplary electric actuator. Furthermore, an exemplary electromagnetic navigation system may be configured to adjust a position and orientation of an exemplary field generator such that a distance between the exemplary field generator and an exemplary electric actuator of the handpiece may be kept at a maximum.

Figure 8:
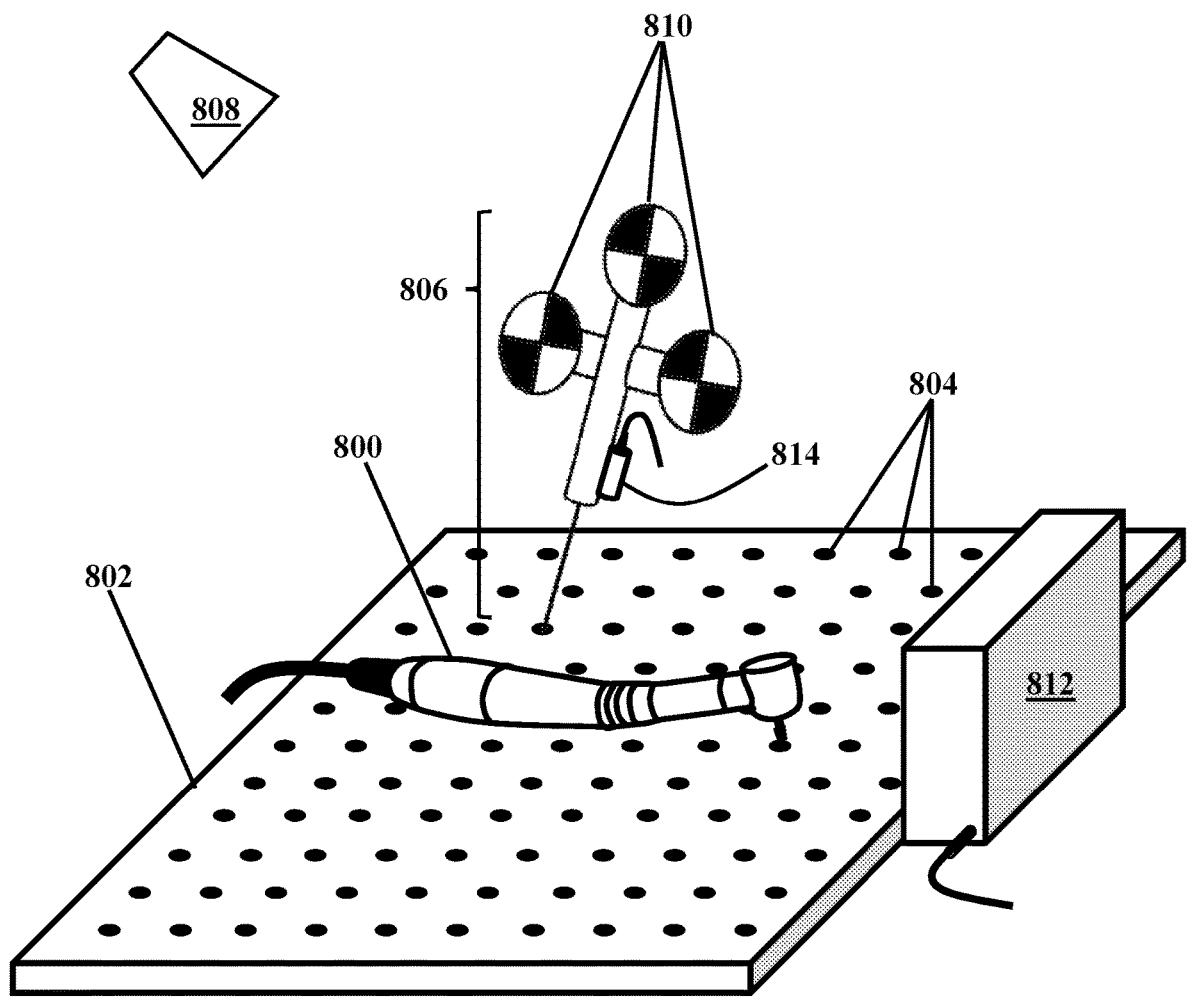
FIG. 8 illustrates a perspective view of a set up for calibration of a mounting position of an electromagnetic sensor on a handpiece, consistent with one or more exemplary embodiments of the present disclosure.

FIG. 8 illustrates a perspective view of a set up for calibration of a mounting position of an electromagnetic sensor on a handpiece 800, consistent with one or more exemplary embodiments of the present disclosure. In an exemplary embodiment, handpiece 800 that may be similar to handpiece 218 may be placed over a calibration plate 802 that may include a plurality of tracking points 804 with known positions. In an exemplary embodiment, an error indicating tool 806 similar to error indicating tool 404 may be utilized to track the locations of plurality of tracking points 804 both by an optical tracking system and an electromagnetic tracking system. In an exemplary embodiment, the optical tracking system may include an optical camera 808 and optical markers 810 mounted on error indicating tool 806. In an exemplary embodiment, an exact position of plurality of tracking points 804 around handpiece 800 may be obtained by tracking optical markers 810 utilizing the optical tracking system. In an exemplary embodiment, electromagnetic tracking system may include a field generator 812 similar to field generator 202 and an electromagnetic sensor 814 similar to second electromagnetic sensor 206b. In an exemplary embodiments, tracked positions of plurality of tracking points 804 around handpiece 800 may be obtained by tracking electromagnetic sensor 814 utilizing the electromagnetic tracking system. In an exemplary embodiment, a tracking error for each tracking point may be obtained by calculating a straight line distance between the exact position of each tracking point and its tracked position. After that, a map of tracking errors for all the tracking points 804 around handpiece 800 may be obtained, and an optimal mounting position for electromagnetic sensor on handpiece 800 may be a position where tracking errors are less than a predetermined threshold. In an exemplary embodiment, the predetermined threshold may be at most 1 mm.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are outlined in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 1001, 1002, or 1003 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. Also, in the preceding Detailed Description, it can be seen that various features are grouped in various implementations. This is for purposes of streamlining the disclosure and is not to be interpreted as reflecting an intention that the claimed implementations require more features than are expressly recited in each claim. Instead, as the following claims reflect, the inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting, and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown or discussed in the present disclosure may be implemented together in any suitable combination. Accordingly, the implementations are not to be restricted except in the light of the attached claims and their equivalents. Also, various modifications and changes may be made within the scope of the appended claims.

What is claimed is:

1. A system for electromagnetic navigation in dental implant placement, the system comprising:
   an electromagnetic tracking system comprising a field generator and configured to track positions and orientations of a plurality of electromagnetic sensors within a tracking volume, the tracking volume encompassing a headrest of a dental unit;
   a passive articulating arm attached to the dental unit from a first end of the passive articulating arm;
   a parallel manipulator comprising:
      a first plate coupled with a second end of the passive articulating arm;
      a second plate, the field generator mounted on the second plate and moveable with the second plate; and
      six prismatic actuators connected between the first plate and the second plate, each prismatic actuator of the six prismatic actuators connected between the first plate and the second plate utilizing two universal joints at either end of each prismatic actuator, the six prismatic actuators configured to move the second plate relative to the first plate with six degrees of freedom; and
   a control unit coupled with the parallel manipulator and the electromagnetic tracking system, the control unit configured to receive tracked positions of the plurality of the electromagnetic sensors from the electromagnetic tracking system and to adjust at least a position or an angular orientation of the field generator, the control unit comprising:
      a processor; and
      a memory configured to store executable instructions to cause the processor to:
         receive coordinates of a volume of interest within the tracking volume with respect to the field generator;
         receive the tracked positions of the plurality of the electromagnetic sensors; and
         urge the parallel manipulator to adjust at least one of the position and the orientation of the field generator based on the tracked positions of the plurality of the electromagnetic sensors, such that the volume of interest encompasses the tracked positions of the plurality of the electromagnetic sensors at any given instant.

2. The system according to claim 1, wherein the passive articulating arm comprises:
   a first arm segment;
   a second arm segment coupled with the first arm segment utilizing an elbow joint, the second arm and the first arm rotatable relative to each other around a single axis of the elbow joint;
   a proximal ball joint coupling the first arm segment with the dental unit, the first arm segment rotatable around the proximal ball joint relative to the dental unit with three rotational degrees of freedom; and
   a distal ball joint coupling the second arm segment with the first plate, the first plate rotatable around the distal ball joint relative to the second arm segment with three rotational degrees of freedom.

3. The system according to claim 2, wherein the passive articulating arm is configured to adjust at least one of a position or an angular orientation of the first plate relative to the headrest.

4. The system according to claim 2, wherein the proximal ball joint comprises a proximal ball stud disposed within a proximal socket attached to the first arm segment, the proximal ball stud attached to the headrest.

5. The system according to claim 2, wherein the distal ball stud comprises a distal ball stud disposed within a distal socket attached to the second arm segment, the distal ball stud attached to the first plate.

6. The system according to claim 1, wherein the plurality of electromagnetic sensors comprises:
   a first electromagnetic sensor mounted in an oral cavity of a patient; and a second electromagnetic sensor mounted on a dental handpiece.

7. The system according to claim 1, wherein each prismatic actuator of the six prismatic actuators comprises an electric prismatic linear actuator.

8. The system according to claim 1, wherein:
tracked positions of an electromagnetic sensor of the plurality of electromagnetic sensors within the tracking volume are associated with tracking errors, and
the volume of interest within the tracking volume corresponds to a region of the tracking volume with the tracking errors less than a predetermined threshold.

9. The system according to claim 8, wherein the tracking errors comprises straight-line distances between tracked positions of an electromagnetic sensor of the plurality of the electromagnetic sensors and corresponding exact positions of the electromagnetic sensor within the tracking volume.

10. The system according to claim 9, wherein the predetermined threshold is at most 1 mm.

11. The system according to claim 9, wherein the predetermined threshold is between 0.5 mm and 0.7 mm.

\* \* \* \* \*